US005541166A

United States Patent [19]

Parish et al.

[11] Patent Number: 5,541,166
[45] Date of Patent: Jul. 30, 1996

[54] SULPHATED POLYSACCHARIDES HAVING ANTI-METASTATIC AND/OR ANTI-INFLAMMATORY ACTIVITY

[75] Inventors: Christopher R. Parish, Macquarie; John M. Snowden, Leeming, both of Australia

[73] Assignee: The Australian National University, Australia

[21] Appl. No.: 853,346

[22] Filed: Mar. 16, 1992

Related U.S. Application Data

[63] Continuation of Ser. No. 391,581, filed as PCT/AU88/00017, Jan. 22, 1988 published as WO88/05301, Jul. 28, 1988, abandoned.

[30] Foreign Application Priority Data

Jan. 23, 1987 [AU] Australia ............... PH9991/87

[51] Int. Cl.$^6$ ................................. A61K 31/725
[52] U.S. Cl. .................. 514/56; 514/54; 514/59; 536/21; 536/53; 536/54; 536/55; 536/55.1; 536/55.3
[58] Field of Search ................ 514/54, 56, 59; 536/21, 53, 54, 55, 55.1, 55.3

[56] References Cited

U.S. PATENT DOCUMENTS

| 4,710,493 | 12/1987 | Landsberger | 514/56 |
|---|---|---|---|
| 4,757,056 | 7/1988 | Van Gorp et al. | 514/54 |
| 4,760,066 | 7/1988 | Busse et al. | 514/264 |
| 4,820,693 | 4/1989 | Gillespie | 514/25 |
| 4,882,318 | 11/1989 | Vlodavsky et al. | 514/56 |

FOREIGN PATENT DOCUMENTS

| 22582/83 | 6/1984 | Australia . |
| 30806/84 | 2/1985 | Australia . |
| 025123 | 3/1981 | European Pat. Off. . |
| 140781 | 5/1985 | European Pat. Off. . |
| 165569 | 12/1985 | European Pat. Off. . |
| 208623 | 1/1987 | European Pat. Off. . |
| 0254067 | 1/1988 | European Pat. Off. . |
| 0251134 | 1/1988 | European Pat. Off. . |
| 1029034 | 5/1966 | United Kingdom . |

OTHER PUBLICATIONS

*The Merck Index*, 9th, 1976, see Monographs 1861, 2212, 2907, 4510 and 4634 at pp. 238, 286, 387, 607, 608, 624.
Patents Abstracts of Japan, C 324, p. 165, JP,A, 60–174729.
Suemasu et al., "Inhibitive Effect of Heparin and Dextran Sulfate on Experimental Pulmonary Metastases,"*Chemical Abstracts*, vol. 73, No. 3 (Jul.20, 1970), p. 209, Abstract 12953h.
Irimura et al., "Chemically Modified Heparins as Inhibitors of Heparan Sulfate Specific Endo–β–glucuronidas (Heparanase) of Metastatic Melanoma Cells", *Biochemistry*, vol. 25 (1986), pp. 5322–5328.
Bar–Ner et al., "Inhibition of Heparitinase Mediated Degradation of Extracellular Matrix Heparan Sulfate by Non Anticoagulant Heparin Species", *Thrombosis Research*, Suppl. VI (1986), p. 117, Abstract No. 231.
Yamamoto et al. *Japan. J. Exp. Med.* 1984, 54 (4), pp. 143–151.
Giroud et al; Therapie 28:889–905 (1973).
Fransson et al: Eur. J. Blochem. 106:59–69 (1980).
Sy et al; Cell. Immunoz. 82:23–32 (1983).
Matzner et al; Thromb. Haemostas, 52(2):134–137 (1984).
Casu et al. Arzneim. Forsch/Drug Res. 36 (I), No. 4: 637–642 (1986).
Castellot, Jr. et al; J. Cell. Biol. 102:1979–1984 (1986).
Matzner et al; Chemical Abstracts 103:3206 of (1985).
Brestel et al; Journal of Immunology 131(5):2515–2519 (1983).
Folkman et al; Science 221: 719–725 (1983).
Sy et al; Cellular Immunology 82:23–32 (1983).
Irimura et al; Biochemistry 25(18):5322–5328 (1986).
Goldberg et al; Anuals of The New York Academy of Science 463(Colloq. Biol. Sci.):289–91 (1986).
Gorelik; Cancer Research 47:809–815 (1 Feb. 1987).
Millar et al; J. Med. 5:23–31 (1974).
Tsubura et al; Gann 67:849–856 (1976).
Tsubura et al; *Cancer Inasion and Metastasls: Biologic Mechanisms and Therapy*, pp. 367–381 (1977).
Suemasu; Gann (Monograph on Cancer Research) 20:163–172 (1977).
Todorutiu et al; Rev. Roum. Morphol. Empryol. Physiol. 24(2):157–160 (1978).
Kobayash et al; Tokushima J. Exp. Med. 26:41–51 (1979).
Yamashita et al; Dev. Oncol. 4(Metastasis) :127–131 (1980).
Drago et al; J. Surg. Onc. 24:33–35 (1983).
Drago et al; Anticancer Research 4:171–172 (1984).
Gorelik et al; Int. J. Cancer 33:87–94 (1984).
Milas et al; Clin. Expl. Metastasis 3(4):247–255 (1985).
Sylvester et al; Proc. West. Pharmacol. Soc. 29:121–123 (1986).
Parish et al; Int. J. Cancer 40:511–518 (1987).
Savion et al; J. Cell. Ansiol. 130:77–84 (1987).
Coombe et al; Int. J. Cancer 39(1):82–88 (1987).

*Primary Examiner*—Douglas W. Robinson
*Assistant Examiner*—Kathleen Kahler Fonda
*Attorney, Agent, or Firm*—Bacon & Thomas

[57] ABSTRACT

A method of anti-metastatic and/or anti-inflammatory treatment of an animal or human patient comprises administration to the patient of an effective amount of at least one sulphated polysaccharide which blocks or inhibits endoglycosidase, particularly heparanase, activity. Suitable sulphated polysaccharides include heparin and modified heparin, fucoidan, pentosan sulphate, dextran sulphate and carrageenan lambda.

4 Claims, 2 Drawing Sheets

SULPHATED POLYSACCHARIDES HAVING ANTI-METASTATIC AND/OR ANTI-INFLAMMATORY ACTIVITY

This application is a CONTINUATION of application Ser. No. 07/391,581, filed as PCT/AU88/00017, Jan. 22, 1988 published as WO88/05301, Jul. 28, 1988, now abandoned.

This invention relates to compounds having anti-metastatic and/or anti-inflammatory activity, and in particular it relates to the use of these compounds as anti-metastatic and/or anti-inflammatory agents in animals and man.

One of the key events in inflammation and tumour metastasis is the adherence of leukocytes or tumour cells to blood vessel walls and their subsequent emigration into tissues. The molecular basis of these processes is poorly understood although it is generally accepted that penetration of the vessel wall requires localised degradation of the interendothelial cell junctions and subendothelial matrix by specific degradative enzymes.

It has now been discovered that certain sulphated polysaccharides can inhibit tumour cell metastasis. While some of these sulphated polysaccharides (such as heparin) exhibit anti-coagulant activity, the anti-metastatic activity appears to be unrelated to their anticoagulant activity, the polysaccharides not inhibiting the attachment of tumour cells to vessel walls but preventing vessel wall penetration. Subsequent studies have revealed that the sulphated polysaccharides block tumour cell-derived endoglycosidases that degrade the subendothelial extracellular matrix (ECM) and allow penetration and passage of tumour cells. In particular, these sulphated polysaccharides have been found to inhibit the action of heparan sulphate specific glycosidase (heparanase) that degrades the heparan sulphate side-chains of the ECM.

Work leading to the present invention has also revealed that continuous infusion of certain sulphated polysaccharides, such as heparin and fucoidan, can completely prevent experimental allergic encephalomyelitis (EAE), an animal inflammatory disease similar to multiple sclerosis in humans.

In a first aspect, the present invention relates to the use of certain sulphated polysaccharides as anti-metastatic and/or anti-inflammatory agents. In this aspect, this invention provides a method of anti-metastatic and/or anti-inflammatory treatment of an animal or human patient, which comprises administration to the patient of an effective amount of at least one sulphated polysaccharide which blocks endoglycosidase activity.

In another aspect, this invention relates to the use of these sulphated polysaccharides in the preparation of pharmaceutical compositions for anti-metastatic and/or anti-inflammatory treatment. In this aspect, there is provided a pharmaceutical composition which comprises at least one sulphated polysaccharide which blocks endoglycosidase activity, together with a pharmaceutically acceptable carrier or diluent therefor.

This invention particularly relates to the use of sulphated polysaccharides which block heparinase activity. Suitable sulphated polysaccharides include heparin, fucoidan, pentosan sulphate, dextran sulphate, and carrageenan-lambda. As previously described, one sulphated polysaccharide which has been found to exhibit endoglycosidase-inhibitory activity is heparin, and in one particularly preferred embodiment of this invention the active component is heparin or a similar sulphated polysaccharide having anti-coagulant activity that has been appropriately modified to reduce this anti-coagulant activity. Examples of such modified polysaccharides are (a) decarboxylated heparin that has a 20 fold reduction in its anti-coagulant activity and negligible loss of anti-metastatic activity and (b) periodate oxidized, reduced heparin that has negligible anti-coagulant activity but is a potent anti-metastatic agent. In both (a) and (b) the endoglycosidase-inhibitory activity of the polysaccharides is retained.

The following Example demonstrates that (a) a range of sulphated polysaccharides can inhibit the metastasis of the mammary adenocarcinoma 13762 MAT; (b) the anti-metastatic activity of the sulphated polysaccharides does not correlate with their anticoagulant activity; and (c) the sulphated polysaccharides do not inhibit adhesion of tumour cells to the vascular endothelium but appear to prevent passaging of tumour cells through the blood vessel wall.

MATERIALS AND METHODS

The following description and examples make reference toward the below listed references which are numbered 1–19. The publications are referred to herein by reference to their corresponding reference numbers as set forth below:

REFERENCES

1. BADENOCH-JONES, P. and RAMSHAW, I. A., *Aust. J. Exp. Biol.Med.Sci*, 63, 91–98 (1985).

2. BRENAN, M. t and PARISH, C. R. *J. Immunol. Meth.*, 74, 31–38 (1984).

3. PARISH, C. R. and SNOWDEN, J. M. *Cell Immunol.*, 91, 201–214 (1985).

4. RAMSHAW, I. A., CARLSEN, S., WANG, H. C., and BADENOCH-JONES, P. *Int.J.Cancer*. 32, 471–478 (1983).

5. REID, L.C.M., Cloning. In: Jakoby, W. B., and Pastan, I. G. (eds). *Methods of Enzymology*. Vol. LVIII, pp 152–164, Academic Press, New York (1979).

6. RICKLES, F. R. and EDWARDS, R. L. *Blood*, 62, 14–31 (1983).

7. SOKAL, R. R. and ROHLF, F. J. *Biometry*. W. H. Freman and Co., San Francisco, p. 770 (1969).

8. WELCH, D. R., NERY, A., and NICOLSON, G. L. *Invas. Metast.* 3, 65–80 (1983).

9. FRANSSON, L-A. *Carbohydr, Res*. 62, 235–244 (1978).

10. LEVVY, G. A. and McALLAN, A. *Biochem, J*. 73, 127–133 (1959).

11. Deibler G. E., R. E. Martinson and M. W. Kies. *Prep. Blochem.* 2: 139 (1972).

12. Panitch H. S. and D. E. McFarlin. *J. Immunol.* 119: 1134. (1977).

13. Farndale R. W., D. J. Buttle and A. J. Barrett. *Biochem.et.Biphys.Acta*. 883: 173. (1986).

14. Welch A., J. H. Holda and R. H. Swanborg. *J. Immunol*. 125: 186. (1980).

15. Hauser S. L., H. L. Weiner, M. Che, M. F. Shapiro, F. Gilles and N. L. Letvin. *J. Immunol.* 132: 1276. (1984).

16. Willenborg D. O. and G. Danta. *Clin. Exp.Neurol*. 21: 225. (1985).

17. Willengborg D. O., P. Sjollema and G. Danta. *Scand. J. Immunol*.23: 75. (1986).

18. Holda J. H. and R. H. Swanborg. *Immun. Commun.* 9: 333. (1980).

19. Hinrichs D. J., C. M. Roberts and F. J. Waxman. *J. Immunol.* 126: 1857. (1981).

EXAMPLE 1

Polysaccharides

Hyaluronic acid (Grade III-S from human umbilical cord), chondroitin-4-sulphate (chondroitin sulphate type A from whale cartilage), chondroitin-6-sulphate (chondroitin sulphate type C from shark cartilage), fucoidan (from *Fucus vesiculosus*), pentosan polysulphate, carrageenan-kappa (Type III from *Eucheuma cottonii*), carrageenan-lambda (Type IV from *Gigartina aciculaire* and *Gigartina pistillata*) were all purchased from Sigma Chemical Co. (St. Louis. Mo). Heparin (mucous) was supplied by Evans Medical Ltd. (Liverpool, U.K.). Heparin CSL was obtained from the Commonwealth Serum Laboratories (Melbourne, Australia). Dextran sulphate (2.3 sulphates/monosaccharide, MW 500,000) was purchased from Pharmacia Fine Chemicals (Uppsala, Sweden) and arteparon (Luitpold Werk, Munich, W. Germany) was a generous gift of Dr P. Ghosh, Royal North Shore Hospital (St. Leonards, Sydney, Australia). The polysaccharides, with the exception of Heparin, CSL, which was purchased as a solution, were dissolved in 0.15M NaCl, in most cases to a stock concentration of 20 mg/ml. Hyaluronic acid and the carrageenans because of their viscosity in solution were dissolved in 0.15M NaCl to concentrations of 10 mg/ml and 2 mg/ml respectively. All polysaccharide solutions were stored at −20°.

Animals and cell lines

Female Fisher F344 inbred rats were bred at the John Curtin School of Medical Research and used at 10 weeks of age.

The 13762 MAT cell line is a mammary adenocarcinoma of Fisher 344 rats adapted to in vitro culture in RPM1 1640 medium (Gibco) supplemented with 10% foetal calf serum (FCS; Flow Labs), 100 units/ml penicillin and 100 ug/ml streptomycin sulphate as described previously (4). These cells are highly metastatic and exhibit stable metastatic properties over a number of passages in culture.

Haematogenic metastases assay

13762 MAT cells were dislodged from the surface of tissue culture bottles by vigorous shaking, the cells were then washed and resuspended in complete medium. $2 \times 10^5$ viable cells in 0.6 mls were injected into the tail vein of Fisher 344 rats. Twelve days after injection the animals were killed, the lungs removed and fixed in Bouins fluid and the number of surface metastatic loci determined. By this injection route metastases are confined to the lung.

Soft agar plating

The plating of cells in soft agar was performed essentially as described by Reid (5). Briefly, an underlayer consisting of 2 mls of 0.5% Difco Bacto-agar in 1640 medium containing 10% calf serum was poured into 60 mm petri dishes (Sterilin, Teddington Middlesex) and allowed to solidify at 4° for 1 h. The cells to be plated were suspended in 0.33% agar in 1640 medium and 10% calf serum and 6 mls of this mixture was poured over the under layer. The plates were first placed at 4° C. for 1 h to allow the agar to solidify and then incubated at 37° in a humidified 5% $CO_2$ atmosphere for 14 days. Colonies are visible after 7–10 days 37° and can be scored at 14 days.

Rosetting assay for cell surface receptors for sulphated polysaccharides

Rosetting assays were carried out in 96-well round-bottomed microplates (Linbro Chemical Co.) and based on a procedure reported earlier (3). 13762 MAT cells were washed and resuspended in phosphate buffered 0.15M NaCl (pH 7) supplemented with 0.1% bovine serum albumin (PBS/BSA). To 25 ul of ice cold 13762 MAT cells ($1 \times 10^6$/ml in PBS/BSA) was added 25 ul of a 1% suspension in PBS/BSA of either washed sheep erythrocytes or sheep erythrocytes coupled with a sulphated polysaccharide using $CrCl_3$ as previously described (3). This mixture was pelleted by centrifugation at 1.000 rpm for 1 min at 4° and left on ice for 1 h no allow the rosettes to stabilize. The cell pellets were then gently resuspended with a short Pasteur pipette and stained with Methyl violet; 50 ul of 0.05% methyl violet being added to the wells. Cell samples were transferred to a haemocytometer chamber and the percentage of rosette-forming cells assessed. A minimum of 100–200 tumour cells were examined for rosettes. A tumour cell with 6 or more erythrocytes attached was considered as a rosette.

Labelling 13762 MAT cells with Hoechst dye No. 33342

Hoechst dye No. 33342 (H33342; Calbiochem-Behring, Kingsgrove. NSW, Australia) was stored at 4° as a stock solution of 600 ug/ml in distilled water. For labelling, 13762 MAT cells were washed and resuspended to a concentration of $5 \times 10^7$ cells/ml in RPM1 1640 medium supplemented with 10% FCS. The cells were transferred to a 37° water bath and 6 ug/ml of H33342 was added. Labelling was continued for 15 min after which the cells were washed twice with cold RPM1 1640 medium and resuspended for injection.

Quantification of tumour cell lodgement

The method used was, similar to that of Brenan and Parish (2). 13762 MAT cells ($2 \times 10^6$) were injected i.v. into rats, in 0.6 ml of RPM1 1640 medium containing either 200 units of CSL heparin (ca 1.6 mg) or 4 mg of chondroitin-4-sulphate. Labelled cells injected in RPM1 1640 alone served as controls. At various times after injection the rats were anesthetized, bled by cardiac puncture and the lungs were removed, washed and placed in saline. Each lung was then minced in PBS and made into a single-cell suspension by gently pressing the tissue fragments through a fine sieve. The cell suspension was centrifuged, washed with PBS and resuspended in 4 ml of PBS. A haemocytometer was used to estimate the number of fluorescent cells within each lung. At least 3 animals were used for each timepoint and each treatment.

Anticoagulate and procoagulent assays

To obtain rat plasma blood was collected by the cardiac puncture of anesthetized rats; nine vole of ran blood being drawn into one volume of 3.8% sodium titrate. The erythrocytes were removed by centrifugation (10,000 g, 4° C.) and the plasma collected and stored at −70° until use.

The effect of the sulphated polysaccharides on the coagulation state of plasma was determined as follows. Polysaccharide, 100 ul diluted in 0.15M NaCl was mixed with 50 ml of normal plasma and 50 ul of 0.15M NaCl and the mixture was warmed at 37° C. for 2 mins. To activate the coagulation pathway either 20 ul of bovine thrombin (Sigma) at a concentration of 30 NIH units/ml in 1.5M NaCl or 20 ul of activated "Thrombofax" reagent-optimized (partial thromboplastin with activator, Ortho Diagnostic Systems Inc.) was added to the mixture. The clotting reaction was then initiated by the addition of 100 ul of 30 mM $CaCl_2$ and the time, in seconds, required for clot formation was recorded. These values were compared to the time taken for plasma to clot in the absence of sulphated polysaccharides. i.e., when the 100 ul of polysaccharide was replaced with 100 ul of saline. The highest concentration of polysaccharide having no detectable effect on the clotting time was taken as the endpoint. The addition of thrombin or "Thrombofax" was necessary to remove the variability introduced by the incomplete activation of the intrinsic pathway that resulted when surface-contact was the only agent activating the coagulation cascade.

A similar assay was used to determine the effect of sulphated polysaccharides on the procoagulant activity of the 13762 MAT cells, To 100 ul of normal rat plasma was added 50 ul of polysaccharide in 0.15M NaCl and 50 ul containing $2 \times 10^4$ 13762 MAT cells in 1640 medium (no serum), After warming for 2 min at 37° 100 ul of 30 mM $CaCl_2$ was added and the time (seconds) for clot formation was measured. The clotting time of plasma when che coagulation cascade was activated by $2 \times 10^4$ 13762 MAT cells in the absence of polysaccharide (the 50 ul of polysaccharide was substituted with 50 ul of saline) served as the control. The highest concentration of polysaccharide that does not produce a detectable increase in the clotting time above that recorded for the controls was the end point. For both assays the effect of each polysaccharide concentration was measured in duplicate and the control values were determined from the mean of at least eight clotting times.

RESULTS

Inhibition of metastasis with sulphated polysaccharides

To test whether sulphated polysaccharides could alter the number of 13762 MAT cell lung metastases the following experiment was performed. Single cell suspensions of 13762 MAT cells ($2 \times 10^5$) were mixed with 4 mg of sulphated polysaccharide in RPM1 1640 medium immediately prior to their injection into the tail vein of rats. Twelve days after injection the numbers of visible surface lung lesions were determined. Although a score of the number of visible lesions does not represent the total number of tumours within the lung it is regarded as a reliable estimate of the extent of metastatic tumour colonization (8).

It is clear from Table I that certain sulphated polysaccharides substantially decreased the number of lung lesions. Heparin was the most effective polysaccharide followed by carrageenan lambda, pentosan sulphate and fucoidan, It was necessary to eliminate the possibility that he apparent antimetastatic effects of the sulphated polysaccharides were caused by their direct toxicity for tumour cells. Accordingly, samples of 13762 MAT cells were incubated for 1 h at 37° with one of each of the sugars shown to inhibit metastasis. After incubation the cells were washed and plated in soft agar. The concentration of cells and sugars was the same as that used for injecting the rats i.e, $3.3 \times 10^5$ cells/6.6 mg sugar/ml or $3.3 \times 10^5$ cells/3.3 mg sugar/ml in the case of the carrageenans. Cells incubated in RPH1 1640 medium alone served as controls. The effect of the sugars on the viability of the tumour cells was assessed from the number of cell colonies visible at 14 days after plating. Dextran sulphate was the only sugar found to reduce either the size or the number of 13762 MAT cell colonies (Table II); the other sugars had no detectable effect on tumour cell viability in vitro, This suggests, with the exception of dextran sulphate, that the reduction in the number of metastases was a consequence of some in vivo action of the polysaccharides. To determine the validity of this interpretation heparin was administered independently of the i.v. injected tumour cells. It was found that the route of heparin injection, whether intraperitoneal, subcutaneous or via another tail vein, did not alter the result. Heparin continued, in each case, to decrease the number of metastases to less than 10% of the control (data not shown); thus, confirming that heparin, at least, was acting in vivo to reduce the number of metastases.

Detection of receptors for sulphated polysaccharides on 13762 MAT cells

Sulphated polysaccharides constitute a major component of the extracellular matrix of endothelial cells, hence it is possible that 13762 MAT cells may adhere to the lung endothelium via receptors for these molecules. To determine whether molecules associated with the surface of 13762 MAT cells bound sulphated polysaccharides a rosetting assay was used.

Sulphated polysaccharides from a variety of sources were coupled to the surface of sheep erythrocytes and the ability of these erythrocytes to attach to 13762 MAT cells was assessed. Uncoupled sheep erythrocytes served as controls. It was found that erythrocytes coupled with the glycosaminoglycans (GAG) chondroitin-4-sulphate and chondroitin-6-sulphate bound strongly to the surface of 13762 MAT cells while chose coupled with hyaluronic acid (a nonsulphated GAG) bound moderately; 77% of the 13762 MAT cells being classified as rosettes (Table III). In contrast, arteparon (an artificially oversulphated GAG from bovine lung) and heparin-coupled erythrocytces bound very poorly to 13762 MAT cells. A similar pattern of selective adhesion was displayed by 13762 MAT cells for erythrocytes coupled with sulphated polysaccharides from non-mammalian sources. Although the carrageenans kappa and lambda bound very strongly to 13762 MAT cells a subpopulation of these cells (ca 32%) consistently did not bind carrageenan lambda. No binding of pentosan sulphate-coupled erythrocytes could be detected and only a subpopulation of 13762 MAT cells (ca 50%) bound rather weakly to dextran sulphate-coupled erythrocytes.

The selective nature of the binding pattern displayed by the 13762 MAT cells indicates that binding is not simply due to the anionic nature of the polysaccharides. For example, the tumour cells reacted strongly with the chondroitin sulphates and yet did not bind heparin a GAG with a much higher charge density. Similarly, hyaluronic acid, a molecule having a relatively low charge density was found to adhere quite strongly to 13762 MAT cells. It can therefore be concluded that 13762 MAT cells possess surface associated molecules (receptors) than bind particular sulphated polysaccharides. There was, however, no positive correlation between the antimetastatic properties of the sugars and their ability to bind to the tumour cell surface (Tables I and III). In fact, with the exception of carrageenan lambda, a negative correlation was evident. This suggests that the antimecastatic activity of the majority of the sulphated polysaccharides could not have been due to the blocking of sulphated polysaccharide specific receptors on the 13762 MAT cell surface.

Anticoagulant activity of the sulphated polysaccharides

13762 MAT cells are known to exhibit procoagulant activity in vitro (1); a property believed to contribute to the metastatic capability of tumour cells by increasing the probability that these cells will become entrapped in the microcirculation of an organ (6). The sugars most effective as antimetastatic agents were found, at quite low concentrations, to both exhibit anticoagulant activity and inhibit the procoagulant activity of the 13762 MAT cells (Table IV). Nevertheless, it is noteworthy that the correlation between antimetastatic and anticoagulant activity is not absolute. Dextran sulphate, for example, inhibited the clotting of plasma at concentrations as low as 1-0.5 ug/ml as did carrageenan lambda (Table 1V) yet carrageenan lambda was substantially more effective at preventing metastasis than dextran sulphate (Table I). Moreover, dextran sulphate was found to impair the viability of the 13762 MAT cells (Table I1) thus, it is probable that the 50% reduction in metastasis observed with this sugar was a reflection of its toxicity. Pentosan sulphate and arteparon similarly exhibited identical endpoints in the anticoagulant assays but differed significantly in their efficacy as antimetastatic agents. It is worth noting that the anticoagulant and procoagulant assays give accurate end points as a narrow range of sugar concentrations can alter plasma from giving coagulation times identical to that of the control to an incoagulable state (data not shown).

Effect of sulphated polysaccharides on the arrest of tumour cells in the lung

Figure 1A:
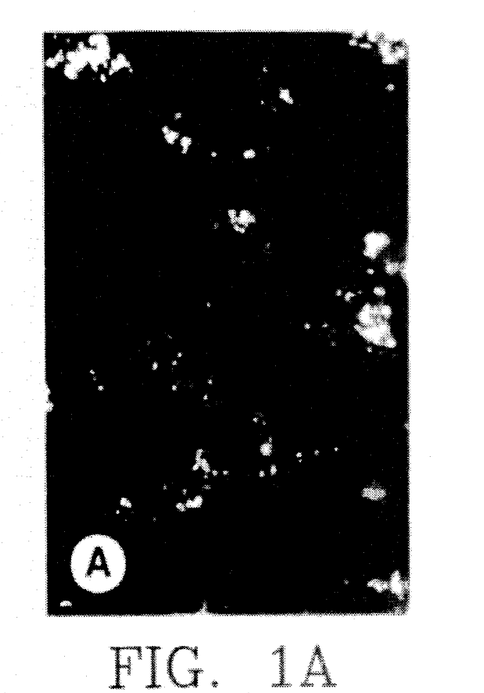
FIG. 1 - Lodgement pattern within the rat lung of i.v. injected, H33342 labelled. MAT cells:. The cells were injected in either saline alone (A and C) or saline containing 1.6 mg heparin (B and D). The pattern of 13762 MAT cell lodgement is shown 15 min (A and B) and 360 min (C and D) after injection. Magnification x55.
Figure 1B:
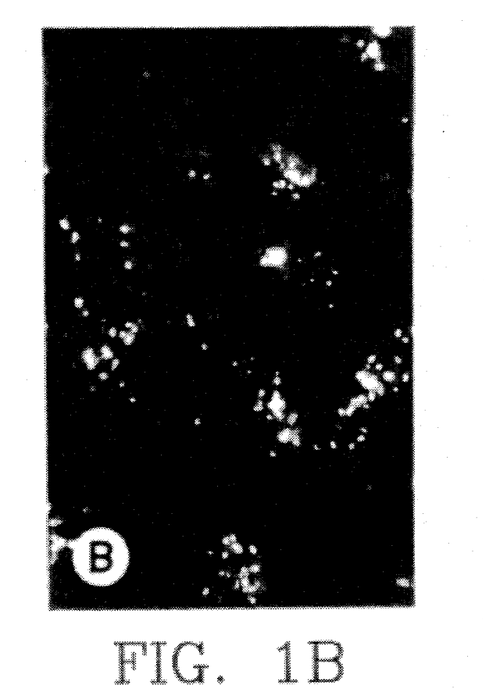
Figure 1C:
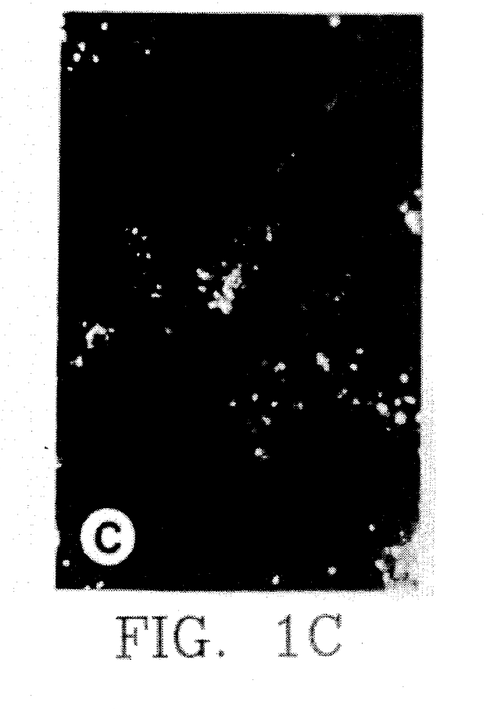
Figure 1D:
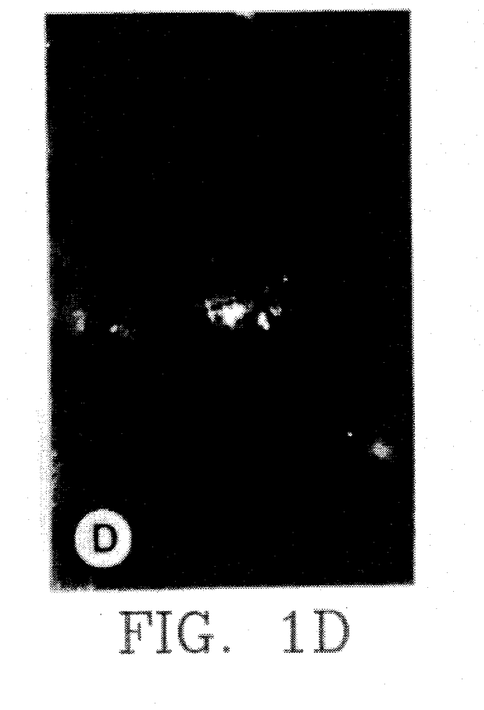

Do the sulphated polysaccharides that reduce metastasis prevent the arrest and/or adhesion of tumour cells to the lung endothelium or do they act at a later stage in the metastatic process? To examine this question the effect of heparin and fucoidan on the arrest, in the lung, of 13762 MAT cells labelled with a fluorescent dye (H33342) was determined. This dye has been used previously to follow lymphocyte recirculation and is reported neither to be toxic nor to modify the cell surface (2). Fluorescently labelled 13762 MAT cells ($2\times10^6$) were injected i.v. in either saline or with fucoidan (4 mg) or heparin (4 mg and 1.6 mg). At 15, 90 or 360 min after injection the rats were bled by cardiac puncture, then killed and the lungs were removed. After washing the lungs were fixed in 5% neutral formalin for 20 h at room temperature. Hand sections of the fixed tissue were examined using low power (100x) fluorescence microscopy. In all cases the cells exhibited a patchy distribution spread throughout the lobes of the lung (FIG. 1a and b) and no qualitative difference in the number of cells arresting after 15 min could be detected. However, the numbers of cells visible in the lung 6 h after injection had declined substantially when heparin or fucoidan had been administered (FIG. 1c and d).

In a subsequent experiment the effect of sulphated polysaccharides on the arrest and lodgement of 13762 MAT cells in the lung yes quantified over a 22 h period. Tumour cells labelled with H33342 were injected with either a sugar, heparin (1.6 mg) or chondroitin-4-sulphate (4mg), or RPM1640 alone, at the times specified (FIG. 2) the numbers of labelled cells remaining in the lungs were estimated. Plasma prepared from the blood samples taken at each time point was used to monitor the the anticoagulant state of the rats. It was found that 1.6 mg of heparin significantly anticoagulated the animals and inhibited the procoagulant activity of the tumour cells for between 3–5 hours. Plasma taken from rats 5 h after the injection of heparin exhibited a clotting pattern indistinguishable from the of normal plasma. Chondroitin-4-sulphate had no effect on the coagulation state of the rats.

Figure 2:
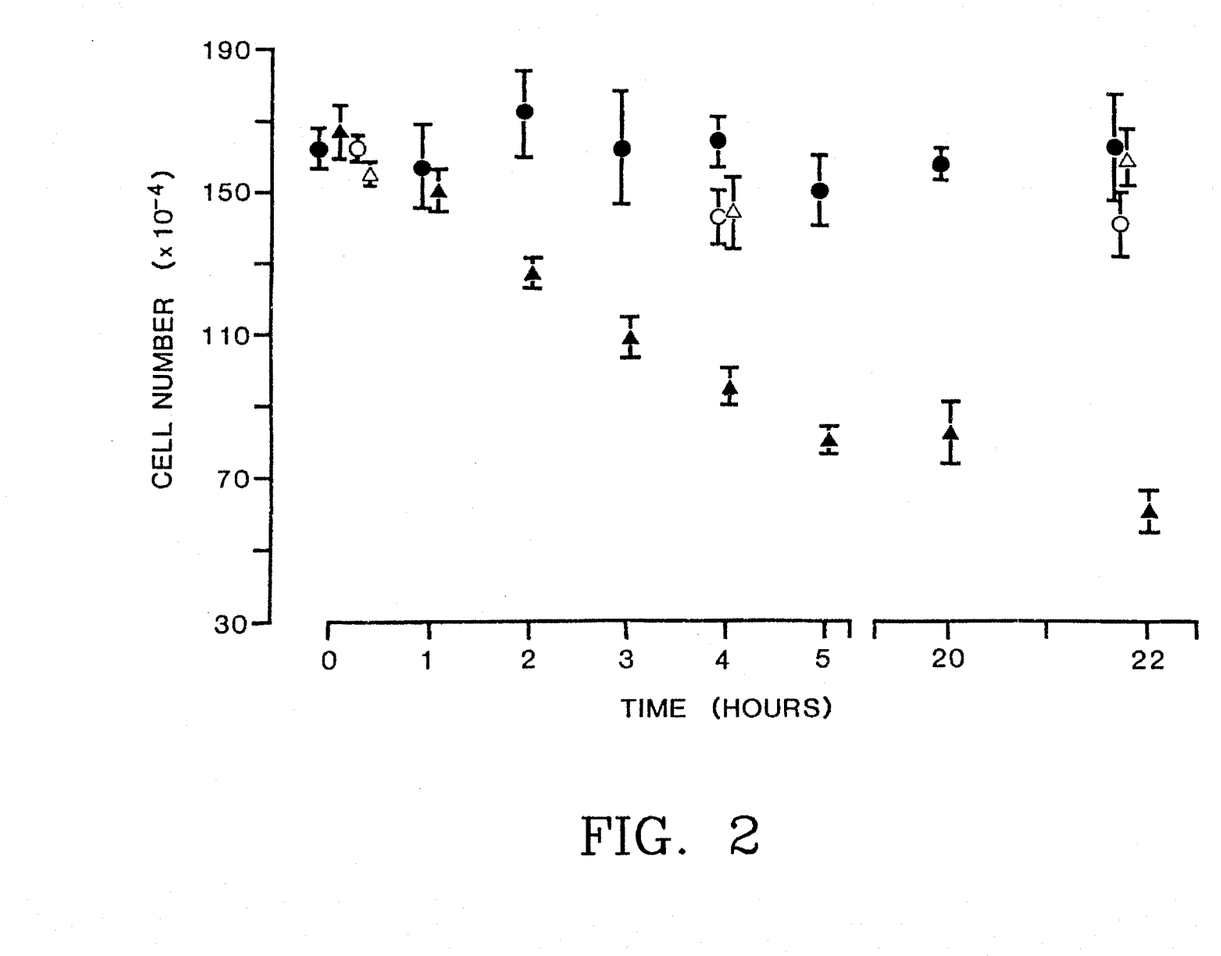
FIG. 2 - Quantitative assessment of the effect of sulphated polyaccharides on the lodgement of H33342 labelled, 13762 MAT cells within the rat lung over a 22 h period. Experiment 1: Cells were injected i.v. in saline alone (●) or saline containing 1.6 mg of heparin (▲). Experiment 2: Cells were injected i.v. in saline alone (○) or saline containing 4 mg of chondroitin-4-sulphate (Δ). The mean and standard error of the number of fluorescent tumour cells within at least 3 replicate rat lungs is given.

The results of this experiment confirmed the qualitative assessment. Heparin did not prevent the initial arrest of the tumour cells but it did increase the rate at which these cells were lost from the lung, such that, after 22 h only 38% of the cells initially arrested could be detected. In contrast, chondroitin-4-sulphate, a sugar having no anticoagulant and antimetastatic activity, had no effect on the retention of tumour cells in the lung (FIG. 2). The displacement of cells from the lung observed with both heparin and fucoidan is thus not due simply to the introduction of a sulphated polysaccharide per se but appears to be more specific. Whether the displacement of cells is due to the anticoagulant effect of the sugar is not clear. However, the data do suggest that the procoagulant activity of the 13762 MAT cells is of little consequence for the initial steps of tumour cell arrest, as heparan and heparin and fucoidan are potent inhibitors of procoagulant activity (Table IV), Effect of the time of heparin administration on its antimetastatic activity The effects of heparin on the number of 13762 MAT cells remaining in the lung first became evident 1–2 hours after injection (FIG. 2). Thus, it could be argued that heparin interferes with the metastatic process after the cells have lodged in the lung capillaries but before penetration of the vascular endothelium. To determine the time of heparin administration most effective in preventing metastases, heparin was given both before and after the tumour cells and the resulting number of lung lesions were recorded.

Heparin most efficiently inhibited metastasis formation when an i.v. injection of tumour cells was immediately followed by an injection of heparin into a different tail vein. However, around 70% inhibition of metastasis could still be achieved if heparin was given up to one hour before or three hours after the tumour cells (Table V). As before the rats were significantly anticoagulated three hours after the heparin injection but after six hours their coagulation state had returned to that of the saline injected controls (data not shown).

Separation of the antimetastatic and anticoagulant effects of heparin

From the data presented above it appears that anticoagulation may not be the complete explanation for the antimetastatic effects of the sulphated polysaccharides. Commercial preparations of sulphated polysaccharides are composed of a heterogeneous set of molecules, different preparations of the same polysaccharide having a slightly different set of molecules. It is therefore possible that heparin batches could vary in their potency as antimetastatic agents, yet possess identical anticoagulation properties. This was found to be the case. Heparin preparations from two different sources had identical anticoagulant properties but differed by approximately 10-fold in their antimetastatic capabilities (Table VI). The quantity of Evans Medical Ltd heparin and CSL heparin required to drop the number of lung metastases by 50% was 0.53 mg and 0.06 mg respectively. These results indicate that the antimetastatic effect is due, at least in part, to some component of heparin distinct from that required for anticoagulation.

TABLE I

THE EFFECT OF SULPHATED POLYSACCHARIDES ON THE METASTASES FORMED BY 13762 MAT CELLS

| Polysaccharide[1] | No Metastases (Mean ± SE)[2] | % of control |
|---|---|---|
| Hyaluronic acid | 295 ± 31 | 100.1 |
| Chondroitin-4-sulphate | 285 ± 27 | 96.5 |
| Chondroitin-6-sulphate | 273 ± 36 | 92.5 |
| Heparin | 30 ± 10 | 10.2* |
| Fucoidan | 96 ± 21 | 32.7* |
| Carrageenan Kappa | 282 ± 29 | 95.6 |
| Carrageenan Lambda | 56 ± 13 | 18.9* |
| Dextran sulphate | 151 ± 21 | 51.1* |
| Pentosan sulphate | 65 ± 13 | 22.0* |
| Arteparon | 139 ± 25 | 47.3* |
| None (control) | 295 ± 25 | |

[1]Four mg of polysaccharide were injected per rat with the exception of both the carrageenans, where 2 mg were injected.
[2]Mean of 5 replicates.
*Significantly different from the control as determined by an analysis of variance followed by an a priori t-test (7). In each case $p < 0.001$.

TABLE II

EFFECT OF SULPHATED POLYSACCHARIDES ON THE VIABILITY OF 13762 MAT CELLS

| Polysaccharide | No. of MAT cell colonies $\bar{x} \pm SE$ |
|---|---|
| Heparin | 333 ± 39 |
| Fucoidan | 330 ± 32 |
| Carrageenan Kappa | 379 ± 12 |
| Carrageenan Lambda | 305 ± 2 |
| Dextran sulphate | 172 ± 27 |
| Pentosan sulphate | 322 ± 3 |
| None (control) | 310 ± 7 |

13762 MAT cells were incubated for 1 h at 37° in polysaccharide (3.3 mg/ml for the carrageenans Kappa and Lambda; 6.6 mg/ml for the others) in 1640 medium before being added to agar and plated out. Four replicate plages were prepared for each sugar.

TABLE III

RECEPTOR STATUS OF 13762 MAT CELLS FOR SULPHATED POLYSACCHARIDES

| Polysaccharide[1] | % of MAT cells forming rosettes[2] |
|---|---|
| Hyaluronic acid | 77 |
| Chondroitin-4-sulphate | 98 |
| Chondroitin-6-sulphate | 74 |
| Heparin | <1 |
| Fucoidan | 5 |
| Carrageenan Kappa | 92 |
| Carrageenan Lambda | 78 |
| Dextran sulphate | 53 |
| Pentosan sulphate | <1 |
| Arteparon | <1 |
| None (control) | <1 |

[1]Polysaccharides were coupled to sheep erythrocytes.
[2]13762 MAT cells possessing 6 or more attached erythrocytes constitute a rosette. Figures given are the average of three separate experiments.

TABLE IV

EFFECT OF SULPHATED POLYSACCHARIDES ON THE COAGULATION STATE OF RAT PLASMA

| Polysaccharide | Anticoagulant activity (µg/ml)[1] APTT | TT | Inhibiton of procoagulant effect of MAT cells (µg/ml)[2] |
|---|---|---|---|
| Hyaluronic acid | >2000 | >2000 | >2000 |
| Chondroitin-4-sulphate | >500 | >5000 | >2000 |
| Chondroitin-4-sulphate | >500 | >5000 | >2000 |
| Heparin | 0.3 | 0.3 | 3 |
| Fucoidan | 1.0 | 1.0 | 20 |
| Carrageenan Kappa | 3.0 | 10.0 | 200 |
| Carrageenan Lambda | 1.0 | 0.3 | 20 |
| Dextran sulphate | 0.3 | 0.3 | 2 |
| Pentosan sulphate | 3.0 | 3.0 | 30 |
| Arteparon | 3.0 | 3.0 | 20 |

[1]Highest concentration of sugar having no decectable effect on plasma coagulation.
[2]Highest concentration of sugar having no inhibitory effect on the procoagulant activity of $2 \times 10^4$ 13762 MAT cells.

TABLE V

EFFECT OF TIME OF HEPARIN ADMINISTRATION ON ITS ANTIMETASTATIC ACTIVITY

| Time (hours) of injection | | Number of Metastases | |
|---|---|---|---|
| 13762 MAT cells[1] | Heparin[2] | (mean ± SE)[3] | % of control |
| 0 | 0 | 7 ± 3 | 2.4 |
| 0 | +1 | 21 ± 4 | 7.1 |
| 0 | +3 | 73 ± 9 | 25.0 |
| 0 | +6 | 202 ± 68 | 69.1 |
| 0 | +22 | 248 ± 48 | 85.2 |
| 0 | No sugar (control) | 291 ± 39 | |
| 0 | 0 | 25 ± 7 | 9.7 |
| +0 | 0 | 82 ± 26 | 31.9 |
| +3 | 0 | 106 ± 6 | 41.7 |
| +6 | 0 | 166 ± 47 | 65.3 |
| +22 | 0 | 272 ± 66 | 106.8 |
| 0 | No sugar (control) | 254 ± 51 | |

[1]$2 \times 10^5$ cells injected i.v.
[2]Each rat received 1.6 mg Heparin i.v.
[3]Mean of at least 3 replicates.

TABLE VI

COMPARISON OF THE ANTIMETASTATIC AND ANTICOAGULANT ACTIVITY OF TWO HEPARIN BATCHES

| Quantity of heparin injected (mg/rat) | No. of metastases (% of control)[1] with: | |
|---|---|---|
| | Evans Medical Ltd heparin | CSL heparin |
| 1.6 | 13.9 ± 6.3 | 10.9 ± 2.2 |
| 0.53 | 45.8 ± 10.8 | 18.5 ± 9.4 |
| 0.18 | 125 ± 20.1 | 24.4 ± 6.2 |
| 0.06 | 135 ± 16.6 | 50.8 ± 3.9 |
| 0.02 | ND | 71.8 ± 10.7 |
| Anticoagulant activity (ug/ml)[2] | | |
| APTT[3] | 0.3 | 0.3 |
| TT[4] | 0.3 | 0.1 |

[1]Mean ± standard error calculated from at least 3 replicates.
[2]Highest concentration of heparin having no detectable effect on plasma coagulation.

TABLE VI-continued

COMPARISON OF THE ANTIMETASTATIC AND ANTICOAGULANT ACTIVITY OF TWO HEPARIN BATCHES

| Quantity of heparin injected (mg/rat) | No. of metastases (% of control)[1] with: | |
|---|---|---|
| | Evans Medical Ltd heparin | CSL heparin |

[3]Activated partial thromboplastin time test.
[4]Thrombin time test.
ND = not determined.

The following Example demonstrates that sulphated polysaccharides block tumour metastasis by inhibiting tumour cell-derived endoglycosidases.

EXAMPLE 2

Table VII presents results from endoglycosidase-inhibition experiments which demonstrate that there is a correlation between the endoglycosidase inhibitory activity of the different sulphated polysaccharides and their ability to inhibit tumour metastasis. Thus, the five polysaccharides that exhibited anti-metastatic activity were comparable inhibitors of tumour cell derived endoglycosidases. In contrast, of the four polysaccharides that failed to inhibit tumour metastasis, three had no detectable endoglycosidase inhibitory activity and one polysaccharide (carrageenan-kappa) was approximately 4–7 times less effective at inhibiting the tumour endoglycosidases as the anti-metastatic polysaccharides.

Although experiments described in Example 1 above suggest that the anticoagulant activity of the sulphated polysaccharides plays little or no role in their antimetastatic activity, it was important to obtain more direct evidence that this is indeed the case. Table VIII presents the results of an experiment in which heparin was separated into anticoagulant enriched and anticoagulant depleted fractions by passage over an anti-thrombin III column (heparin exerts its anticoagulant activity by interacting with anti-thrombin III in plasma). Approximately 40% of the heparin preparation used in this experiment bound to the anti-thrombin III column and was eluted with 2M NaCl (termed high affinity heparin). It was found that the heparin fractions with high and low affinity for anti-thrombin III had identical endoglycosidase-inhibitory activity, almost identical anti-metastatic activity (comparable to unfractionated heparin) but differed approx. 300–500 fold in their anticoagulant activity. Such a result clearly indicates that the anticoagulant activity of heparin plays little or no role in the anti-metastatic properties of the polysaccharide.

In additional experiments attempts were made to chemically modify heparin such that the anticoagulant activity of the polysaccharide was destroyed but the anti-metastatic activity of the molecule retained. Such procedures (i) eliminate the undesirable anticoagulant properties of heparin if it is to be used clinically as an anti-metastatic and anti-inflammatory drug and (ii) unlike anti-thrombin III fractionation, provide a commercially viable approach for preparing an effective drug. The results obtained with two chemically modified preparations of heparin, which are virtually devoid of anticoagulant activity, are presented in Table IX. Both preparations exhibited substantial anti-metastatic activity although they were less effective than unmodifed heparin.

TABLE VII

Ability of Different Sulphated Polysaccharides to Inhibit Tumour Cell Derived Endoglycosidases

| Polysaccharide | Inhibits Tumour Metastasis | Endoglycosidase Inhibitory Activity (µg/ml)[1] |
|---|---|---|
| Hyaluronic acid | − | >50 |
| Chondroitin-4-sulphate | − | >50 |
| Chondroitin-6-sulphate | − | >50 |
| Carrageenan-kappa | − | 10 |
| Carrageenan-lambda | + | 1.5 |
| Dextran sulphate | + | 1.6 |
| Fucoidan | + | 2.8 |
| Pentosan sulphate | + | 2.4 |
| Heparin | + | 1.5 |

[1]Concentration of polysaccharide required to produce a 50% inhibition of degradation of the extracellular matrix ($^{35}SO_4$-labelled) of endothelial cells by 13762 MAT cells.

TABLE VIII

Biological Activity of Heparin Fractions with High and Low Affinity for Anti-Thrombin III

| Heparin Fraction | Anticoagulant Activity (µg/ml)[1] | | Endoglycosidase Inhibitory Activity (µg/ml)[2] | Number of metastases (% control)[3] |
|---|---|---|---|---|
| | APTT | TT | | |
| Unfractionated | 0.25 | 1.5 | 1.5 | 6.3% |
| High affinity heparin[4] | 0.13 | 0.75 | 2.3 | 7.7% |
| Low affinity heparin[4] | 62 | 250 | 2.0 | 17.6% |

[1]Highest concentration of polysaccharide having no detectable effect on plasma coagulation. APTT - activated partial thromboplastin time test, TT - thrombin time test.
[2]Concentration of polysaccharide producing a 50% inhibition of degradation of the extracellular matrix of endothelial cells by 13762 MAT cells.
[3]$2 \times 10^5$ MAT cells injected i.v. into each rat with 2 mg of each heparin fraction and number of lung metastases quantified 12 days later.
[4]Heparin separated into fractions with high and low affinity for anti-thrombin III by passage through an anti-thrombin III coupled column.

Preparation of Chemically Modified Heparins

Heparin was periodate oxidized and potassium borohydride reduced based on the method of Fransson (9). Heparin (10 mg/ml, bovine lung) in 50 mM sodium phosphate buffer, pH 7.0, containing 40 mM sodium periodate was incubated at 37° C. in the dark for 20 hr. The reaction was stopped by the addition of D-mannitol (5 mg/ml). Low molecular weight reaction products were removed by dialysis against distilled water. The oxidized heparin was then reduced by the addition of 20 mg/ml of $KBH_4$ and incubation for 3 hr at 20° C. Excess borohydride was decomposed by the addition of 20 µl/ml of glacial acetic acid. The oxidized and reduced heparin was precipitated twice at 4° C. by the addition of 2 vols ethanol and finally redissolved in 0.15M NaCl.

N-desulphated heparin was prepared by heating the material in 0.04M HCl at 100° C. for 90 min. N-acetylated heparin was obtained by treatment of N-desulphated heparin with acetic anhydride as previously described (10).

TABLE IX

Anti-Metastatic Activity of Chemically Modified Heparins with Negligible Anticoagulant Activity

| Polysaccharide[1] | Number of Metastases[2] (mean ± SE) | % of control |
| --- | --- | --- |
| N-acetylated heparin | 158 ± 24 | 43.8 |
| No Polysaccharide (control) | 360 ± 54 | |
| Periodate-oxidised heparin | 214 ± 35 | 43.6 |
| Unmodified heparin | 95 ± 10 | 19 |
| No Polysaccharide (control) | 491 ± 30 | |

[1]Chemically modified heparins had <0.1% anticoagulant activity of unmodified heparin.
[2]Metastasis experiment as in Table VIII.

The following Example demonstrates the anti-inflammatory activity of the sulphated polysaccharides, heparin, fucoidan and pentosan sulphate.

EXAMPLE 3

MATERIALS AND METHODS

Rats. Lewis (RT-1[1]) rats were bred at the John Curtin School of Medical Research. Both males and females of 8–10 weeks of age were used. In each experiment controls and experimental rats were matched for sex.

Induction of EAE.

Active. Guinea pig BP was prepared according to the method of Deibler et at (11) and BP in saline was emulsified in an equal volume of incomplete Freund's adjuvant containing 4 mg/ml added *Mycobacterium butyricum*. Rats received 0.1 ml emulsion in one footpad of both hind feet. Total dose received was 50 μg BP and 400 μg *Mycobacterium butyricum*.

Passive. Cells for passive transfer were generated following the method of Panitch and McFarlin (12) Single cell suspensions were prepared from spleens of donor rats sensitized 12 days previously with BP-CFA as described above. Cells were cultured at $2\times10^6$/ml in RPHI 1640 +5% fetal calf serum, $5\times10^{-5}$M 2-mercaptoethanol, 200 mH L-glutamine and penicillin and streptomycin. Con A was added at 2 μg/ml and cultures were incubated at 37° C. in an atmosphere of 10% $CO_2$, 7% $O_2$ and the balance $N_2$. Cells were harvested after 72 hrs, washed with Hanks balanced salt solution (BSS) and transferred to recipients via a lateral tail vein. All transfer populations contained $30\times10^6$ viable cells.

Evaluation of clinical EAE

Clinical EAE was graded according to the following scheme: 0, asymptomatic; 1, flaccid distal half of tail; 2, entire tail flaccid; 3, ataxia, difficulty in righting; 4, hind limb weakness; 5, hind limb paralysis.

In most experiments we also calculated the mean day of onset of disease (MDO), the mean clinical score (NCS) and the mean length or duration of disease (MLD). Values are expressed standard error of the mean.

Histology

Rats were perfused with 10% neutral buffered formalin. Their spinal cords removed and prepared by standard histological techniques. Slides were stained with H and E.

Polysaccharides

Chondroitin-4-sulfate, fucoidan (from *Fucus vesiculosus*), pentosan polysulfate and heparin (sodium salt from bovine lung) were all purchased from Sigma (St. Louis, Mo.). The polysaccharides were dissolved in 0.15M NaCl and stored at −20° C. They were thawed and then boiled for 2 min immediately before use.

Heparin devoid of anticoagulant activity was prepared by periodate oxidation and borohydrate reduction using a similar procedure to that described by Fransson (9). Bovine lung heparin (10 mg/ml) was dissolved in 0.05M sodium phosphate buffer, pH 7.0, containing 40 mH sodium periodate and left to react for 18 hrs at 37° C. in the dark. The reaction was stopped by the addition of solid D-mannitol (5 mg/ml) and the solution then dialyzed against distilled water at room temperature for 2 hrs, the dialysate being changed every 30 min. The oxyheparin was then reduced by the addition of solid potassium borohydride (2 mg/mg heparin), the reduction reaction being left for 3 hrs at room temperature and then terminated by the addition of glacial acetic acid (1 μl/mg of borohydride). The heparin was then ethanol precipitated twice (2 vole ethanol, 4° C., 18 hrs) and finally dissolved in 0.15MH NaCl to a concentration of 20 mg/ml. Approximately 50% of the heparin was recovered as the periodate oxidised borohydride reduced preparation.

The anticoagulant activity of heparin and periodate oxidized heparin was determined using rat plasma in the activated partial thromboplastin time and thrombin time tests. Based on these assays periodate oxidation resulted in a 500–2000 fold reduction in the anticoagulant activity of heparin.

Delivery of sulfated polysaccharides. Because of the short half life of some of the polysaccharides in vivo we thought it necessary to give repeated doses. We first attempted ip injections of heparin every twelve hours. Unfortunately, this produced unacceptable levels of hemorrhage and even death of some animals. We chose therefore to use mini osmotic pumps (type 2 ML, ALZA Corp, Palo Alto, Calif.) which were implanted subcutaneously in the back. The pumps have a 2 ml capacity and deliver approximately 10 μl/hr for 7 days. Plasma levels of heparin was measured in rats implanted with an osmotic pump containing 20 mg/ml. The method employed was essentially the dimethylmethylene blue procedure of Farndale et al (13). A steady state concentration of 10–20 μg/ml was reached by 24 hrs after implanting the pump on day 0 and no heparin was detectable on day 8, i.e. 24 hrs after the pump ceased to deliver.

RESULTS

Recipient rats received $30\times10^6$ EAE effector cells and at the same time osmotic pumps were placed subcutaneously in the back. The pumps contained 2 ml of heparin at either 10 mg/ml or 20 mg/ml. As shown in Table X there was a degree of protection in both heparin treated groups. Only 3 of 6 rats receiving 10 mg/ml heparin developed disease and only 1 of 5 receiving 20 mg/ml. In the latter case, the one animal which did develop disease did so later after cell transfer and also exhibited a milder disease.

In the next experiment we used heparin again as well as three further sulfated polysaccharides, fucoidan, chondroitin-4-sulfate, and pentosan sulfate, and also asked if initiation of treatment could be delayed for 3 days and still provide protection. Fucoidan as well as heparin gave complete protection against EAE even when treatment was delayed till day 3 after cell transfer (Table XI). Pentosan sulfate gave partial protection as evidenced by later onset, milder clinical disease, and shorter duration of disease. Chondroitin-4-sulfate had no protective effect.

Often, therapeutic studies of various agents in EAE demonstrate that clinical disease may be abrogated, yet histopathologic examination will reveal quite extensive inflammatory lesions (14, 15). To examine this in the present context, 3 control and 3 heparin treated animals from the experiment described in Table XI were killed on day 8 post cell transfer and examined for inflammatory lesions. Virtually every low power field of a 2 cm longitudinal section through the lower thoracic/upper lumbar cord of control rats had numerous perivascular inflammatory lesions.

In contrast, no lesions were seen in any of 80 sections from the same area of the three heparin treated rats.

To determine if the sulfated polysaccharides are inhibiting adoptive EAE by simply killing the transferred cells, we examined the ability of treated rats to exhibit memory to a challenge with BP-CFA. We (16–17) and others (18–19) have reported that following recovery from passively induced EAE, or in the case of neonates, in the absence of any initial disease symptoms following cell transfer (16–17), a later active challenge with BP-CFA leads to a much earlier onset of disease symptoms than is seen in control animals which never received EAE effector cells. The interpretation of these data is that early onset is the result of activation of memory cells which persist in the animal and arise from the original transfer population. Therefore, the animals represented in Table XI were challenged with 50 g BP-CFA on day 14 after receiving the cell transfer. Control rats which had never received cells were also challenged. The results are shown in Table XII. Naive animals developed disease day 10–11 after active immunization. Cell recipients on the other hand showed a memory response following challenge irrespective of treatment regimen or presence or absence of initial clinical signs, thus demonstrating that treatment did not inhibit adoptively transferred disease by killing the cells.

Is the effect that heparin, and possibly the other polysaccharides have on adoptively transferred EAE a function of their anticoagulant activity? To answer this question, anticoagulant free heparin was prepared by periodate oxidation and borohydride reduction as described in MATERIALS AND METHODS and then tested for its EAE inhibiting activity. As seen in Table XIII, all animals receiving anticoagulant free heparin developed EAE; however, there was a significant delay in onset of disease, a diminution in the clinical severity and also a decrease in the duration of the disease symptoms. These results strongly suggest that the EAE inhibiting effect of heparin is not due solely to its anticoagulating activity.

The effect of heparin on actively induced EAE was also examined and the results presented in Table XIV. When heparin treatment was begun at the time of sensitization there was a significant delay in the onset of disease, however, the clinical score attained or the duration of disease did not differ from controls animals. It is interesting to note that the delay of 6 days is approximately the length of time the pumps deliver heparin, 7 days.

TABLE X

Effect of heparin on adoptively transferred EAE[a]

| Treatment | # Rats with EAE/ Total | Mean Day of Onset | Mean Clinical Score |
|---|---|---|---|
| Control | 4/4 | 4.3. ± 0.2 | 3.9 ± 0.1 |
| Heparin[b] (10 mg/ml) | 3/6 | 5.3 ± 0.3[c] | 3.5 ± 0.2[c] |
| Heparin[b] (20 mg/ml) | 1/5 | 7.0[c] | 2.5[c] |

[a]$30 \times 10^6$ Con A incubated EAE spleen cells given iv.
[b]Heparin given in osmotic pumps placed subcutaneously at time of cell transfer.
[c]Represent the score only for the animal(s) which developed clinical signs.

TABLE XI

Effect of sulfated polysaccharides on adoptively transferred EAE

| Treatment | # With EAE/ Total | Mean Day Onset | Mean Clinical Score | Mean Length Disease |
|---|---|---|---|---|
| Control | 7/7 | 4.4 ± 0.2 | 4.1 ± 0.9 | 5.0 ± 0.4 |
| Heparin (20 mg/ml) | 0/8 | — | — | — |
| Fucoidan (20 mg/ml) | 0/6 | — | — | — |
| Chondroitin-4-sulfate (20 mg/ml) | 5/5 | 5 | 3.5 ± 0.2 | 5.0 ± 0.4 |
| Pentosan sulfate (20 mg/ml) | 5/5 | 6.2 ± 0.3 | 2.4 ± 0.2 | 3.0 ± 0.4 |

[a]Osmotic pumps containing sulfated polysaccharides were implanted day 3 after cell transfer.

TABLE XII

Memory response in rats receiving sulfated polysaccharides 3 days after adoptive transfer of EAE effector cells

| Treatment Group | # With EAE/ # Challenged[a] | Individual Day of Onset |
|---|---|---|
| Naive | 4/4 | 10, 11, 11, 11 |
| Control (cells only) | 4/4 | 7, 7, 7, 8 |
| Neparin | 5/5 | 7, 7, 7, 8, 8 |
| Fucoidan | 6/6 | 7, 7, 8, 8, 8, 10 |
| Chondroitin-4-sulfate | 5/5 | 7, 7, 8, 8, 10 |
| Pentosan sulfate | N.D.[b] | N.D. |

[a]Rats challenged with 50 μg BP-CFA on day 14 after initial cell transfer.
[b]Not determined.

TABLE XIII

Effect of anticoagulant-free heparin on passively induced EAE

| Treatment | # With EAE/ Total | Mean Day Onset | Mean Clinical Score | Mean Duration Disease |
|---|---|---|---|---|
| Control | 7/7 | 5.0 | 3.4 ± 0.1 | 4.0 ± 0.2 |
| Heparin | 0/5 | — | — | — |

TABLE XIII-continued

Effect of anticoagulant-free heparin on passively induced EAE

| Treatment | # With EAE/ Total | Mean Day Onset | Mean Clinical Score | Mean Duration Disease |
| --- | --- | --- | --- | --- |
| (20 mg/ml) Periodate-oxidised heparin (20 mg/ml) | 5/5 | 6.4 ± 0.2 | 1.6 ± 0.2 | 2.4 ± 0.4 |

TABLE XIV

Effect of heparin on actively induced EAE

| Treatment | # With EAE/ # Challenged | Mean Day Onset | Mean Clinical Score | Mean Duration Disease |
| --- | --- | --- | --- | --- |
| Control | 5/5 | 11.4 ± 0.5 | 4.2 ± 0.3 | 6.6 ± 0.6 |
| Heparin[a] (20 mg/ml) | 5/5 | 17.6 ± 0.8 | 5.0 | 6.0 ± 0.5 |

[a]Heparin pumps implanted at time of sensitization with 50 μg BP-CFA/rat.

We claim:

1. A method of anti-metastatic treatment of an animal or human patient in need of such treatment, which comprises administration to the patient an anti-metastatic effective amount of sulphated polysaccharide which blocks or inhibits endoglycosidase activity, said sulphated polysaccharide being periodate-oxidized, reduced heparin.

2. A method of anti-inflammatory treatment of an animal or human patient in need of such treatment, which comprises administration to the patient an anti-inflammatory effective amount of a sulphated polysaccharide which blocks or inhibits endoglycosidase activity, said sulphated polysaccharide being selected from the group consisting of fucoidan and periodate-oxidized, reduced heparin.

3. A method according to claim 2, wherein said sulphated polysaccharide is fucoidan.

4. The method according to claim 2, wherein said sulfated polysaccharide is periodate-oxidized, reduced heparin.

* * * * *